(12) United States Patent
Koehler

(10) Patent No.: US 8,765,180 B2
(45) Date of Patent: Jul. 1, 2014

(54) COMPOSITION COMPRISING CALCIUM CARBONATE AS A WHITE PIGMENT

(75) Inventor: Klaus Koehler, Frederiksberg (DK)

(73) Assignee: Chr. Hansen A/S, Hoersholm (DK)

( * ) Notice: Subject to any disclaimer, the term of this patent is extended or adjusted under 35 U.S.C. 154(b) by 73 days.

(21) Appl. No.: 13/143,475

(22) PCT Filed: Dec. 28, 2009

(86) PCT No.: PCT/EP2009/067952
§ 371 (c)(1),
(2), (4) Date: Aug. 26, 2011

(87) PCT Pub. No.: WO2010/079103
PCT Pub. Date: Jul. 15, 2010

(65) Prior Publication Data
US 2011/0305759 A1 Dec. 15, 2011

(30) Foreign Application Priority Data
Jan. 7, 2009 (EP) .................................... 09000088

(51) Int. Cl.
*A61K 9/36* (2006.01)
(52) U.S. Cl.
USPC ........... 424/479; 424/687; 426/103; 426/540; 426/93

(58) Field of Classification Search
None
See application file for complete search history.

(56) References Cited

U.S. PATENT DOCUMENTS

| | | | |
|---|---|---|---|
| 4,844,934 A | 7/1989 | Lueddecke et al. |
| 5,571,547 A | 11/1996 | Serpelloni et al. |
| 6,500,473 B1 | 12/2002 | Koehler et al. |
| 2002/0026886 A1 | 3/2002 | Isager et al. |
| 2005/0152851 A1 | 7/2005 | Kaminski |
| 2008/0113076 A1 | 5/2008 | Klingenberg |
| 2009/0010857 A1* | 1/2009 | Waterfield ................. 424/52 |

FOREIGN PATENT DOCUMENTS

| | | |
|---|---|---|
| EP | 0 239 086 B1 | 6/1992 |
| EP | 1 300 394 B1 | 2/2004 |
| EP | 1 066 761 B1 | 9/2004 |
| EP | 1 875 814 A1 | 1/2008 |
| EP | 1 964 479 A1 | 9/2008 |
| EP | 1 967 081 A1 | 9/2008 |
| EP | 2 011 835 A1 | 1/2009 |
| EP | 1 471 151 B1 | 11/2009 |
| JP | 11-43430 | 2/1999 |
| WO | WO 99/03449 | 1/1999 |
| WO | WO-02/08182 A1 | 1/2002 |
| WO | WO-2006/032339 A1 | 3/2006 |
| WO | WO-2007/003543 A1 | 1/2007 |
| WO | WO-2007/009601 A1 | 1/2007 |
| WO | Wo-2007/090614 A1 | 8/2007 |
| WO | WO 2009/007273 A2 | 1/2009 |

OTHER PUBLICATIONS

International Search Report PCT/EP2009/067952 dated Mar. 24, 2010.
S. Drusch et al., "Microencapsulation properties of two different types of n-octenylsuccinate-derivatised starch", Eur Food Res Technol (2006) 222:155-164.
Thomas E. Furia, "Colour Additives in Food", CRC Handbook of Food Additives, Jan. 1, 1981, CRC Press, 612-613.
Anonymous, "Speciality starches provide superior emulsification and encapsulation", Jan. 21, 2004, pp. 1-2 retrieved from the internet, XP002569407.
E.B. Jackson, "Sugar Confectionery Manufacture", Second Edition, Blackie Academic and Professional, 1995.
J. Smith et al., "Food Additives Data Book", 2003, Blackwell Science Ltd. XP002524085, pp. 304-306.
Database WPI Week 200646, XP002465172, Jun. 22, 2006.

* cited by examiner

*Primary Examiner* — Hasan Ahmed
(74) *Attorney, Agent, or Firm* — Foley & Lardner LLP

(57) ABSTRACT

A white coloring composition comprising calcium carbonate as a white pigment. It may be used in the manufacture of food and pharmaceutical products.

17 Claims, No Drawings

COMPOSITION COMPRISING CALCIUM CARBONATE AS A WHITE PIGMENT

FIELD OF THE INVENTION

The present invention relates to a white colouring composition comprising calcium carbonate as a white pigment. It may be used in the manufacture of food and pharmaceutical products.

BACKGROUND ART

Commercially is today used titanium oxide as a white pigment in different food products.

Titanium oxide is e.g. used for panning confectionary products in order to make a coating with the white colouring pigment.

As known in the art panning involves building up a layer of closely knit sugar crystals around the outside of a preformed centre (e.g. a chewing gum base) by spraying a syrup on the centres in a specially designed panning machine. A panned coating may be a process where many fine layers are applied to the preformed centre and then dried.

For further details see e.g. page 328 of the textbook of E. B. Jackson with title "Sugar Confectionary Manufacture" (ISBN 0 7514 0197 8).

When one uses pigments (e.g. titanium oxide) in a panning process a suitable composition comprising that pigment is mixed with the syrup and this syrup/pigment mixture is then used for the panning.

In U.S. Pat. No. 5,571,547 (column 5, lines 51-57) is mentioned that a syrup suitable for panning e.g. a chewing gum may comprise calcium carbonate as pigment. Calcium carbonate is simply mentioned as an example in a list of examples that also comprises titanium oxide.

None of the working examples of U.S. Pat. No. 5,571,547 use calcium carbonate as white pigment—all examples use titanium oxide as the white pigment.

Titanium oxide is today widely used as a white pigment in the panning process for white colouring of confectionary products such as chewing gums or chocolate lentils.

To our knowledge calcium carbonate is today not used commercially in a significant way as a white pigment in a panning process for white colouring a confectionary product such as chewing gums or chocolate lentils.

Without being limited to theory, it is believed that one reason for this may be that some of the today used compositions are not giving good results (no good/acceptable white colouring) when calcium carbonate is used as a white pigment in a panning process.

Another use of titanium oxide is whitening of fat reduced foods like low fat salad dressings and low fat mayonnaise.

To our knowledge calcium carbonate is today not used commercially in a significant way as a white pigment in such fat reduced foods.

Without being limited to theory, it is believed that one reason for this may be that some of the today used compositions are not giving good results (no good/acceptable white colouring) when calcium carbonate is used as a white pigment in fat reduced foods.

Titanium oxide is used even though many commercial providers would like to use other white pigments. One reason for this is that titanium oxide is also used in paint (e.g. paint for painting e.g. a wall) and since it is used for paint it can imply some negative consumer "feelings" in relation to edible products.

JP 11 04330 (Eisai, 1999) essentially relates to a special sugar coated riboflavin tablet. The sugar coat includes a pigment and a binder. Numerous examples of suitable pigments are mentioned such as e.g. Titanium oxide, silicon dioxide and calcium carbonate. Further are mentioned numerous examples of suitable binders—such as e.g. polyvinyl pyrrolidone, hydroxypropyl cellulose and gum Arabic). In working example 1 is used calcium carbonate and gum Arabic as binder.

Accordingly, gum Arabic is in JP 11 04330 NOT used as a hydrocolloid (dispersing agent) but as a glue/binder—i.e. as it is well known that gum Arabic may be used as a glue on stamps. It is well known that many of the other mentioned examples of binders (e.g. polyvinyl pyrrolidone, hydroxypropyl cellulose) can not be used as a hydrocolloid (dispersing agent) as discussed herein.

The article (S. Dursch, K. Schwarz: Microencapsulation properties of two different types of n-octenylsuccinate-derivatised starch, European food research and technol., vol. 222, 20 Oct. 2005 pages 155-164) described use of starch octenyl succinate derivative (n-OSA starch) for micro-encapsulation of fish oil. The n-OSA starch may be said to be used as an emulsifier for a liquid/liquid system (i.e. fish oil drops in a water phase). In this article, it is not described nor suggested to use the n-OSA starch as a dispersing agent in a solid/liquid suspension [e.g. in a suspension of a solid pigment (e.g. calcium carbonate) in a water phase].

International PCT application with application number PCT/EP2008/058447 was filed 1 Jul. 2008. Applicant is Chr. Hansen A/S and it was NOT PUBLISHED at the 7 Jan. 2009 priority date of this present application.

PCT/EP2008/058447 describes a water-dispersible composition comprising at least solid pigment and at least 5 wt % of at least one starch octenyl succinate derivative as a hydrocolloid (see e.g. claim 1 and 14).

The water-dispersible composition as described herein also uses octenyl succinate derivative as a hydrocolloid.

PCT/EP2008/058447 does not explicitly mention calcium carbonate as an example of a pigment.

SUMMARY OF THE INVENTION

The problem to be solved by the present invention is to provide a pigment composition that is not using titanium oxide as pigment and still give a comparable acceptable white colouring of a product of interest such as e.g. chewing gums or chocolate lentils.

The solution is based on the fact that the present inventor has identified that a water-dispersible composition using starch octenyl succinate derivative as a hydrocolloid is very good in relation to use of calcium carbonate as a white pigment—see working example herein for further details.

As can be seen in reference example 3 herein—for instance gum Arabic is NOT working satisfactory for calcium carbonate—i.e. one may say that starch octenyl succinate derivative works surprisingly well.

One advantage of using calcium carbonate instead of titanium oxide as the white pigment is that absolutely no herein relevant negative health concerns are associated with calcium carbonate.

Accordingly, as compared to titanium oxide (see discussion above) there should not be any negative consumer "feelings" in relation to use of calcium carbonate as pigment in e.g. edible confectionary products.

Accordingly, a first aspect of the invention relates to a water-dispersible composition comprising from 5% to 70% of calcium carbonate particles with an average particle diameter of less than 10 μm as a white pigment and from 0.5% to 50% of at least one starch octenyl succinate derivative as a hydrocolloid.

An example of a composition of the first aspect is shown in working Example 1 herein—wherein the composition comprises 38% w/w of calcium carbonate and 10% w/w of starch octenyl succinate derivative as a hydrocolloid. The rest of the material/substance of the composition/suspension of Example 1 herein was liquid (Propylene glycol: 26%; water: 26%).

Accordingly, as understood by the skilled person and as a normal standard for compositions as described herein—the percentage of the different material/substances of the composition (e.g. calcium carbonate and/or starch) are calculated as w/w percentage.

As evident to the skilled person—the composition of first aspect may be dried to remove water and other relevant liquid like e.g. Propylene glycol).

If e.g. done for the composition/suspension of Example 1 herein one could get a composition essentially free of the liquids and it would give a dried (e.g. powder) composition comprising around 80% w/w of calcium carbonate and around 20% w/w of starch octenyl succinate derivative.

A second aspect of the invention relates to a method for preparing the water-dispersible composition of the first aspect, said method comprising the preparation of a suspension of calcium carbonate by comminuting the solid pigment in an aqueous media in the presence of at least 0.5 wt % of hydrocolloid.

The term "comminuting" shall be understood as the skilled person would understand it the present context—i.e. that the term relates to that one makes smaller particles in order to get particles with the average particle diameter of less than 10 μm as required in the first aspect.

As known to the skilled person—calcium carbonate used as starting material to make the suspension generally comprise particles (e.g. agglomerated granulates) with a particle size significantly bigger than having a diameter of 10 μm.

The process of transforming e.g. such agglomerated granulates into smaller particles may be done/performed by simple mixing using the herein described very good dispersing properties of the starch octenyl succinate derivative (see e.g. working Example 1 herein for an example of this).

The term "comminuting" may also be a so-called milling of herein relevant particles.

A third aspect of the invention relates to use of the water-dispersible composition of the first aspect for white colouring an edible or pharmaceutical product.

DEFINITIONS

All definitions of herein relevant terms are in accordance of what would be understood by the skilled person in relation to the herein relevant technical context.

The term "pigment" relates to a material that changes the colour of light it reflects as the result of selective colour absorption. This physical process differs from fluorescence, phosphorescence, and other forms of luminescence, in which the material itself emits light.

The term "white pigment" simply relates to a pigment that gives a white colour. When used as a pigment as described herein calcium carbonate will always give a white colour and the term "white" in relation to use of calcium carbonate as described herein may therefore be seen as merely descriptive—i.e. not a limiting term.

The term "white colouring" in relation to the use of the water-dispersible composition as described herein simply relates to the fact that the calcium carbonate pigment gives a white colour.

Embodiment of the present invention is described below, by way of examples only.

DETAILED DESCRIPTION OF THE INVENTION

Water-Dispersible Composition

Beside the calcium carbonate (as a white pigment) and the starch octenyl succinate derivative (as a hydrocolloid) the water-dispersible composition as described herein may of course comprise other herein relevant material/substances.

As evident to the skilled person, when there herein is described relevant percentage (%) of e.g. calcium carbonate (as a white pigment) and octenyl succinate derivative (as a hydrocolloid) the sum of such percentages can of course not exceed 100% in the water-dispersible composition as described herein.

The water-dispersible composition may be dried. Accordingly, it may have a water content of less than 5% based on the total composition or it may have a water content of less than 1% based on the total composition.

As discussed—after drying the ratio of the w/w percentage of calcium carbonate (as a white pigment) and octenyl succinate derivative (as a hydrocolloid) will of course be changed accordingly.

Accordingly, a separate aspect of the invention relates to a dried water-dispersible composition comprising from 40% to 98% of calcium carbonate particles with an average particle diameter of less than 10 μm as a white pigment and from 1% to 50% of at least one starch octenyl succinate derivative as a hydrocolloid.

In a preferred embodiment, the dried water-dispersible composition comprises from 60% to 98% of calcium carbonate particles with an average particle diameter of less than 10 μm as a white pigment and from 5% to 40% of at least one starch octenyl succinate derivative as a hydrocolloid.

Alternatively, the water-dispersible composition may have a water content of more than 5% based on the total composition.

Calcium Carbonate

In a preferred embodiment the water-dispersible composition of first aspect comprises from 10% to 50% of the calcium carbonate particles, more preferably from 15% to 50% of the calcium carbonate particles.

In a preferred embodiment the average particle diameter of the calcium carbonate particles is less than 5 μm, more preferably the average particle diameter of the calcium carbonate particles is less than 1 μm.

In some preferred situations the average particle diameter of the calcium carbonate particles is less than 200 nm.

Starch Octenyl Succinate Derivative

As discussed above, the water-dispersible composition as described herein comprises from 0.5% to 50% of at least one starch octenyl succinate derivative as a hydrocolloid.

Starch octenyl succinate is the common name given to starch n-octenyl succinate which is made by treating starch with n-octenyl succinic anhydride at pH 8-8.5. This type of starch derivative is anionic due to a carboxyl group and hydrophobic due to the $C_8$-alkene chain.

One exemplary starch octenyl succinate derivatives is designated an E-number, E1450 (see European Union (EU) food additive legislation), which represents starch sodium octenyl succinate.

Preferably, starch octenyl succinate derivatives having a degree of substitution (D.S.) up to 0.11, more preferably up to 0.03 are used within the present invention.

It is assumed that the hydrocolloid acts as a protective colloid, which prevents agglomeration of the pigments and that it provides wetting and dispersing activity.

In a preferred embodiment the water-dispersible composition of first aspect comprises from 4% to 50% of the at least one starch octenyl succinate derivative as a hydrocolloid, more preferably it comprises from 4% to 30% of the at least one starch octenyl succinate derivative as a hydrocolloid.

It a suitable example it comprises from 8% to 25% of the at least one starch octenyl succinate derivative as a hydrocolloid.

According to the art—a herein suitable example of starch octenyl succinate derivative may be termed n-OSA starch (alternatively termed NOSA starch).

A Method for Preparing the Water-Dispersible Composition

As discussed above, the second aspect of the invention relates to a method for preparing the water-dispersible composition as described herein, said method comprising the preparation of a suspension of calcium carbonate by comminuting the solid pigment in an aqueous media in the presence of at least 0.5 wt % of hydrocolloid.

As evident to the skilled person one may make adequate adjustments of the method in order to get a specific water-dispersible composition of interest—for instance to get a composition with 10% of the starch octenyl succinate derivative hydrocolloid.

Further, if one e.g. wants a dried composition the method may comprise the further step of reducing the water content in said suspension to less than 5%.

Use of the Water-Dispersible Composition

As discussed above, the third aspect of the invention relates to use of the water-dispersible composition as described herein to white colouring of an edible or pharmaceutical product.

Essentially, this use may herein be seen as corresponding to know prior art uses of water-dispersible compositions comprising other pigments such as e.g. titanium oxide.

Accordingly, it is herein not required in details to describe how such compositions are used for colouring of a herein relevant edible or pharmaceutical product—the skilled person knows how to use it in relation to obtainment of specific objectives (e.g. degree of colouring) of interest.

In a suitable example the water-dispersible composition is used in a coating for the product, such as e.g. when the product is a pharmaceutical tablet product.

A herein preferred embodiment is wherein the product is a confectionary product and wherein the coating is made by panning.

Example of herein commercially relevant products is chewing gum or chocolate lentil.

As known in the art and as already discussed above—the process of panning may be described as comprising building up a layer of knit sugar crystals around the outside of a preformed centre (e.g. a chewing gum base) by spraying a syrup on the centres in a panning machine, wherein there the calcium carbonate composition as described herein is added to the syrup before spraying the syrup on the centres.

For chewing gum it may many times be that the coating made by panning the composition as described herein is the white coating that one "sees" in the final product—since chewing gum many times is white.

When the product is chocolate lentils the coating may many times be a layer on which the final colour (e.g. a blue colour) is applied.

Another herein relevant use is wherein the product is a fat reduced food, such as a low fat salad dressing or a low fat mayonnaise.

A reason for using a white pigment composition in such low fat products is that when the products comprises low amounts of fat they may get a transparent look and consumers may prefer a more white look for such products.

EXAMPLES

Example 1

In the laboratory a product according to the invention was produced:

| Ingredient | Amount |
| --- | --- |
| Purity Gum 2000 (NOSA starch) National Starch and Chemical Company Bridgewater, NJ 08807 USA | 10.0 grams |
| Propylene glycol | 26.0 grams |
| Calofort U (precipitated calcium carbonate) Specialty Minerals Lifford, Lifford Lane, Kings Norton, Birmingham B30 3 JW, England | 38.1 grams |
| Demineralised water | 26.1 grams |

All ingredients were weighed and mixed in a glass beaker with a magnetic stirrer After mixing the blend was treated for approx. 5 minutes in a Silverson L4R (Silverson Machines Ltd, Waterside, Chesham, Bucks., England, HP5 1PG.

A viscous white liquid was obtained

Example 2

In the laboratory the product produced as described in Example 1 was tested as follows.

First a sugar syrup was produced from the following ingredients:

| Ingredient | Amount |
| --- | --- |
| Sucrose | 340.0 grams |
| Maltodextrin | 10.0 grams |
| Water | 150.0 grams |
| Total | 500.0 grams |

The ingredients were weighed in a tared pot, mixed and heated until all the ingredients were dissolved.

Water was added up to 500 grams to compensate for evaporation loss of water during heating.

Brix level was checked to be 70.0+/−0.5 before the syrup was used.

5% of the product described in Example 1 was dissolved in the syrup.

With a brush one and two layers of the syrup with the calcium carbonate preparation were applied on a dark piece of cardboard.

After drying overnight the syrup containing the calcium carbonate preparation in both cases (one and two layers) had turned into a nice white layer.

Example 3

This example is a comparative example using gum Arabic as a dispersing agent. In this example was used exactly the same ingredients in the same amount expect gum Arabic had replaced the NOSA starch—i.e. a true comparative example.

| Ingredient | Amount |
|---|---|
| Gum Arabic | 10.0 grams |
| Propylene glycol | 26.0 grams |
| Calofort U (precipitated calcium carbonate) Specialty Minerals Lifford, Lifford Lane, Kings Norton, Birmingham B30 3 JW, England | 38.1 grams |
| Demineralised water | 26.1 grams |

All ingredients were weighed and mixed in a glass beaker with a magnetic stirrer After mixing the blend was treated for approx. 5 minutes in a Silverson L4R (Silverson Machines Ltd, Waterside, Chesham, Bucks., England, HP5 1PG.

A viscous white liquid was obtained

The products of the table above were tested as in Example 2.

With a brush one and two layers of the syrup with the calcium carbonate preparation were applied on a dark piece of cardboard.

Contrary to the product with NOSA starch—the syrup with the product with gum Arabic did NOT give a nice white layer (neither one nor two layers) after drying overnight.

Accordingly, the results of this comparative example clearly demonstrated that NOSA starch works significantly better than gum Arabic.

REFERENCES

1: Textbook of E. B. Jackson with title "Sugar Confectionary Manufacture" (ISBN 0 7514 0197 8).
2: U.S. Pat. No. 5,571,547
3: PCT/EP2008/058447. Applicant is Chr. Hansen A/S

The invention claimed is:

1. A water-dispersible composition comprising from 5% to 70% of calcium carbonate particles with an average particle diameter of less than 10 μm as a white pigment and from 0.5% to 50% of starch sodium octenyl succinate as a hydrocolloid, wherein the composition is an ingredient for a food_product or a pharmaceutical product.

2. The water-dispersible composition of claim 1, wherein the average particle diameter of the calcium carbonate particles is less than 1 μm.

3. The water-dispersible composition of claim 1, wherein it comprises from 4% to 50% of starch sodium octenyl succinate as a hydrocolloid.

4. The water-dispersible composition of claim 3, wherein it comprises from 4% to 30% of starch sodium octenyl succinate as a hydrocolloid.

5. The water-dispersible composition of claim 1, wherein it comprises from 20% to 50% of the calcium carbonate particles.

6. A dried, water-dispersible composition comprising from 40% to 98% of calcium carbonate particles with an average particle diameter of less than 10 μm as a white pigment and from 1% to 50% of starch sodium octenyl succinate as a hydrocolloid.

7. A method for preparing the water-dispersible composition of claim 1, comprising the preparation of a suspension of calcium carbonate by comminuting the solid pigment in an aqueous media in the presence of at least 0.5 wt % of hydrocolloid, wherein the hydrocolloid is starch sodium octenyl succinate.

8. A food or pharmaceutical product that comprises the water-dispersible composition of claim 1 for white colouring.

9. The product of claim 8, wherein the water-dispersible composition is used in a coating for the food or pharmaceutical product.

10. The product of claim 9, wherein the product is a confectionary product and wherein the coating is made by panning.

11. The product of claim 10, wherein the confectionary product is a chewing gum.

12. The product of claim 10, wherein the confectionary product is a chocolate lentil.

13. The product of claim 9, wherein the product is a pharmaceutical tablet product.

14. The product of claim 8, wherein the product is a fat-reduced food.

15. The product of claim 14, wherein the fat-reduced food is a low-fat salad dressing or a low-fat mayonnaise.

16. The product of claim 10, wherein said panning comprises building up a layer of knit sugar crystals around the outside of a preformed centre by spraying a syrup on the centres in a panning machine, and wherein the water-dispersible composition comprises from 5% to 70% of calcium carbonate particles with an average particle diameter of less than 10 μm as a white pigment and from 0.5% to 50% of starch sodium octenyl succinate as a hydrocolloid that is added to the syrup before spraying the syrup on the centres.

17. The water-dispersible composition of claim 1, wherein the composition does not contain titanium oxide.

* * * * *